US011224594B2

(12) United States Patent
Stenzler et al.

(10) Patent No.: US 11,224,594 B2
(45) Date of Patent: Jan. 18, 2022

(54) NICOTINE FORMULATIONS AND METHODS OF MAKING AND USING THE SAME

(71) Applicant: Philip Morris Products S.A., Neuchatel (CH)

(72) Inventors: Alex Stenzler, Long Beach, CA (US); Noe Zamel, Ontario (CA); Arthur Slutsky, Ontario (CA); Steven Ellis, Ontario (CA); Steve Han, Huntington Beach, CA (US)

(73) Assignee: Philip Morris Products S.A., Neuchâtel (CH)

( * ) Notice: Subject to any disclaimer, the term of this patent is extended or adjusted under 35 U.S.C. 154(b) by 0 days.

(21) Appl. No.: 14/856,129

(22) Filed: Sep. 16, 2015

(65) Prior Publication Data

US 2017/0071929 A1 Mar. 16, 2017

(51) Int. Cl.

| | |
|---|---|
| ***A24B 15/18*** | (2006.01) |
| ***A61K 31/465*** | (2006.01) |
| ***A61K 9/00*** | (2006.01) |
| ***A61K 45/06*** | (2006.01) |
| ***A24F 42/20*** | (2020.01) |

(52) U.S. Cl.

CPC ............ *A61K 31/465* (2013.01); *A24F 42/20* (2020.01); *A61K 9/0075* (2013.01); *A61K 45/06* (2013.01)

(58) Field of Classification Search

None

See application file for complete search history.

(56) References Cited

U.S. PATENT DOCUMENTS

| | | | | |
|---|---|---|---|---|
| 5,746,227 | A | 5/1998 | Rose et al. | |
| 6,102,036 | A * | 8/2000 | Slutsky | A61M 15/0045 128/202.21 |
| 6,234,169 | B1 | 5/2001 | Bulbrook et al. | |
| 6,799,576 | B2 | 10/2004 | Farr | |
| 8,182,838 | B2 | 5/2012 | Morton et al. | |
| 8,256,433 | B2 | 9/2012 | Gonda | |
| 8,381,739 | B2 | 2/2013 | Gonda | |
| 8,440,231 | B2 | 5/2013 | Smyth et al. | |
| 8,668,934 | B2 | 3/2014 | Vehring et al. | |
| 8,689,803 | B2 | 4/2014 | Gonda | |
| 8,741,348 | B2 | 6/2014 | Hansson et al. | |
| 2001/0026788 | A1 * | 10/2001 | Piskorz | A61K 9/0073 424/46 |
| 2003/0103908 | A1 | 6/2003 | Piskorz | |
| 2006/0178394 | A1 | 8/2006 | Staniforth et al. | |
| 2007/0292519 | A1 | 12/2007 | Piskorz | |
| 2008/0020048 | A1 | 1/2008 | Snape et al. | |
| 2008/0138399 | A1 * | 6/2008 | Gonda | A24F 47/002 424/450 |
| 2009/0068276 | A1 | 3/2009 | Main et al. | |
| 2011/0082076 | A1 | 4/2011 | Dellamary et al. | |
| 2011/0268809 | A1 | 11/2011 | Brinkley et al. | |
| 2012/0042886 | A1 | 2/2012 | Piskorz | |
| 2012/0138056 | A1 | 6/2012 | Morton et al. | |
| 2012/0321717 | A1 * | 12/2012 | Staniforth | A61K 31/485 424/490 |
| 2013/0098377 | A1 | 4/2013 | Borschke et al. | |
| 2013/0209540 | A1 | 8/2013 | Duggins et al. | |
| 2013/0323179 | A1 | 12/2013 | Popov et al. | |
| 2014/0166027 | A1 | 6/2014 | Fuisz et al. | |
| 2014/0190496 | A1 | 7/2014 | Wensley et al. | |
| 2014/0212504 | A1 | 7/2014 | Weers et al. | |
| 2014/0234392 | A1 | 8/2014 | Hansson et al. | |
| 2015/0031609 | A1 | 1/2015 | Steiner et al. | |
| 2015/0283070 | A1 | 10/2015 | Stenzler et al. | |
| 2015/0344456 | A1 * | 12/2015 | Dull | A61P 3/04 514/343 |

FOREIGN PATENT DOCUMENTS

| | | | |
|---|---|---|---|
| CA | 2146954 | | 10/1996 |
| CA | 2265198 | | 9/1999 |
| CN | 1298294 | A | 6/2001 |
| CN | 105828819 | A | 3/2016 |
| JP | 2003-519175 | A | 6/2003 |
| JP | 2004-515467 | A | 5/2004 |
| JP | 2014-522880 | A | 9/2014 |
| KR | 20100069333 | A | 6/2010 |
| WO | WO 94/17679 | A1 | 8/1994 |
| WO | WO 99/45902 | A1 | 9/1999 |
| WO | WO 01/049274 | A1 | 7/2001 |
| WO | WO 2002/011695 | A2 | 2/2002 |
| WO | WO 2004/093848 | A2 | 11/2004 |
| WO | 2005/107872 | | 11/2005 |
| WO | WO 2008/069970 | A2 | 6/2008 |
| WO | WO 2013/021199 | A2 | 2/2013 |

(Continued)

OTHER PUBLICATIONS

Benowitz et al., 2009, "Nicotine Chemistry, Metabolism, Kinetics and Biomarkers. Hanb. Ex. Pharmacol.," (192): 29-60.

International Preliminary Report on Patentability, issued by the International Bureau of WIPO for PCT/US2016/051961, dated Mar. 29, 2018; 10 pgs.

Yinjiao, "Hazards of Smoking and Nicotine Replacement Therapy," *Adverse Drug Reactions Journal*, Oct. 31, 2008;10(5):346-351, English Abstract: 6 pgs.

Chinese Office Action dated Jun. 4, 2018 by the Chinese Patent Office for corresponding application CN 201510717550.X; Including English Translation; 23 pgs.

Jones T.E. and Williams, "Craving control using nicotine replacement therapy in a teaching hospital," *Internal Med J*, Mar. 20, 2012; 42(3): 317-322.

(Continued)

*Primary Examiner* — Robert T. Crow
*Assistant Examiner* — John P Nguyen
(74) *Attorney, Agent, or Firm* — Mueting Raasch Group

(57) ABSTRACT

A method of reducing nicotine cravings is described. The method includes inhalation of a dry powder formulation containing a dose of nicotine by a subject seeking nicotine cravings reduction. The formulation includes amounts and concentrations of nicotine that are significantly lower than cigarettes or nicotine replacement therapies.

17 Claims, 7 Drawing Sheets

(56) References Cited

FOREIGN PATENT DOCUMENTS

| | | | |
|---|---|---|---|
| WO | WO 2014/033437 | A2 | 3/2014 |
| WO | WO 2015/057603 | A1 | 4/2015 |
| WO | 2015/166344 | | 11/2015 |
| WO | 2015/166350 | | 11/2015 |
| WO | WO 2015/173648 | A2 | 11/2015 |
| WO | WO 2016/118328 | A1 | 7/2016 |
| WO | WO 2017/048974 | A1 | 3/2017 |

OTHER PUBLICATIONS

Russian Office Action issued in application No. RU2018113272 by the Russian Patent Office; dated Dec. 28, 2018: 14 pgs., including English Translation.

European Search Report issued by the European Patent Office for EP Application No. 16847313.0, dated Mar. 26, 2019; 9 pgs.

Russian Office Action issued by the Russian Patent Office for RU Application No. 2018113272, dated May 20, 2019; 17 pgs.

First Examination Report issued for EP Application No. 16847313.0, by the European Patent Office, dated Feb. 14, 2020; 7 pgs.

Japanese Office Action for JP Application No. 2018-514457, issued by the Japanese Patent Office dated Mar. 1, 2021; 22 pgs.

* cited by examiner

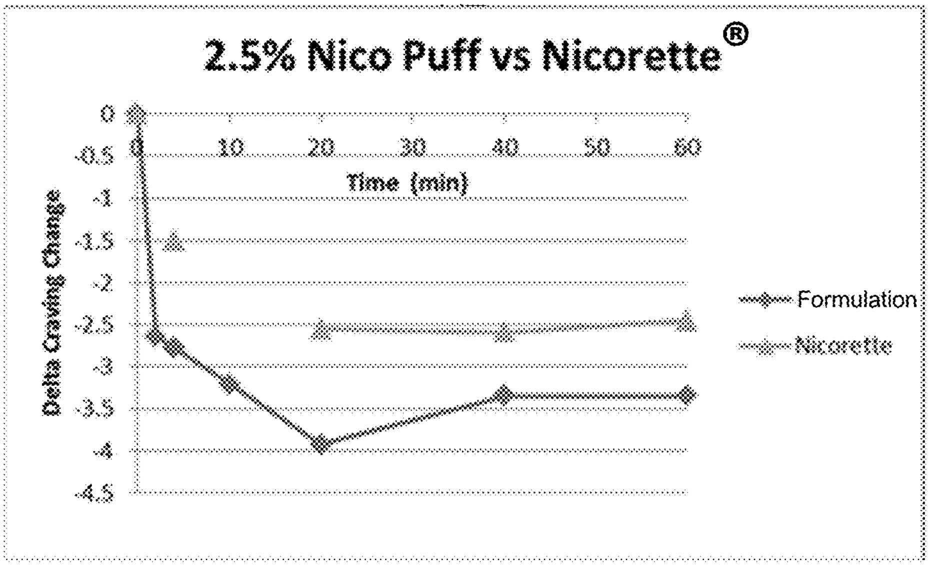
Figure 4A
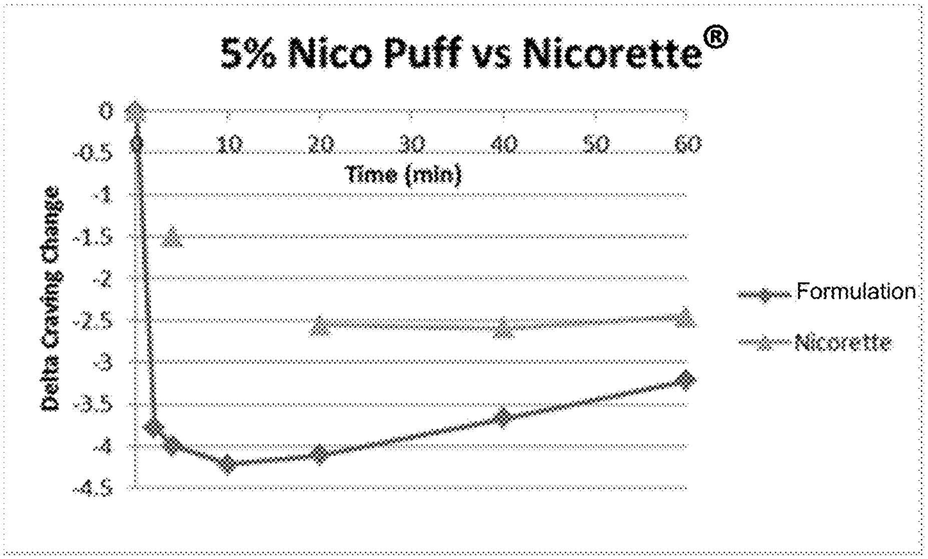
Figure 4B
Figure 4

| | 1 | 2 | 3 | 4 | 5 | 6 | 7 | 8 | 9 | 10 |
|---|---|---|---|---|---|---|---|---|---|---|
| Seconds | 3.6 | 3.35 | 3.58 | 4.76 | 4.41 | 3.28 | 4.83 | 8.36 | 6.8 | 2.68 |

NICOTINE FORMULATIONS AND METHODS OF MAKING AND USING THE SAME

BACKGROUND OF THE INVENTION

Smoking has been determined to be a contributory or causative factor in a number of diseases including respiratory diseases such as emphysema, chronic bronchitis, lung infections and lung cancer, but also in various cardiac pathologies. Most regular smokers become addicted to, or dependent upon, the pharmacological effects of nicotine in tobacco smoke. Generally, the physical manifestation of nicotine addiction is described as the cravings for smoking, or more specifically, as nicotine cravings.

A common strategy in overcoming nicotine addiction in general, and nicotine cravings in particular, is the mimicking of cigarette smoking's effects, followed by gradual reduction and, eventually, by complete elimination. The most important and immediate effect of smoking is the absorption of nicotine into the smoker's blood, an effect which can be effectively mimicked by the administration of nicotine doses. By gradually reducing the doses, until complete elimination, nicotine addiction can be treated.

The level of nicotine concentration in the blood of the smoker is a factor considered in designing a nicotine replacement therapy. People who are addicted to nicotine, usually from smoking cigarettes or other tobacco leaf products, typically require high blood levels of nicotine to satisfy their craving for nicotine. As demonstrated in FIG. 1, typical peak venous blood levels of nicotine following the inhalation of a single cigarette reaches 10-15 ng/mL. To attain those blood levels using dry powder formulations containing nicotine, formulations need up to 30% nicotine with a minimum of 8% nicotine, as demonstrated in FIG. 1 and further described for example in U.S. Patent Application Publication No. 2007/0292519. While inhaling this powder at 28% nicotine concentration delivers nicotine blood levels comparable to those attained by smoking a cigarette, a 30% nicotine composition is generally harsher to inhale, and the high blood level it produces may in fact reinforce rather than reduce the addiction to nicotine. Other dry powder formulations of nicotine used, and delivery approaches to match blood levels associated with cigarette smoking in order to attain nicotine craving reduction, have been described in the art, for example by U.S. Pat. Nos. 6,799,576, 8,256,433 and 5,746,227. Typical formulations in the art contain nicotine bound to excipients, i.e. each and every particle of the formulation would comprise nicotine and excipients.

The period of time it takes from nicotine delivery to the lungs until a given nicotine blood concentration is achieved is also an important factor to be considered in designing a particulate nicotine formulation for delivery by inhalation. Various forms of non-inhaled nicotine delivery attempted to match the kinetics of achieving cigarette blood levels of nicotine with varied success. For example, the kinetics curve of nicotine uptake via non-inhalation typically takes typically 20-30 minutes. Many of these nicotine replacement products are therefore not found to adequately satisfy the nicotine craving of smokers, which is reflected in the high failure rate of smoking cessation attempts.

While nicotine uptake via inhalation is much faster (typically 10-20 seconds) than non-inhalation routes, there are several other drawbacks to traditional, inhalable nicotine formulations. For example, size distribution of the particles used is a factor to be considered if the nicotine replacement therapy is centered on inhaled delivery of a dry particulate formulation. It is believed that cigarette smoke contains approximately 4000 chemical compounds and has a range of particle sizes from less than 0.1 micron to approximately 0.5 micron to hundreds of micron in diameter. During inhalation, it is known that most particles larger than 10-12 micron in size typically can't make the turn in the oral cavity to enter the lower respiratory tract and instead impact the back of the throat. While particles less than 5 micron in size are generally considered respirable and can thus enter the lower respiratory tract, the majority of particles less than 1 micron in size do not settle in the alveoli, and are thus expelled during subsequent exhalation. Consequently, exhaled particles of this size range (less than about 1 micron) are commonly characterized as "second hand smoke." The state of the art in the development of products designed to replace traditional cigarettes, is to replicate or match the particles found in cigarettes. For example, such replacement technologies include e-cigarettes that produce nicotine vapor, ultrasonically produced nicotine aerosol droplets or nicotine oral sprays. These replacement cigarette technologies typically produce particles that are less than 0.5 micron in size, and very large particles that are greater than 10-12 micron in size. However, each of these technologies suffer from the same result—not all of the inhaled nicotine and associated compounds remain in the lungs and the balance is either exhaled into the environment or ingested. Unfortunately, this means that the public must still contend with the same problem of users of these technologies producing what is effectively second hand smoke, and accordingly these technologies are increasingly being banned in selected public spaces.

Thus, there is a need in the art for inhalable dry powder nicotine formulations and methods of use that can more quickly and consistently satisfy nicotine cravings while delivering an overall lower concentration of nicotine into the bloodstream. Ideally, such formulations and methods of use would uniquely target particle retention within the airways of the lungs while reducing or eliminating exhalable nicotine by a subject. The present invention satisfies these needs.

SUMMARY OF THE INVENTION

A method of reducing nicotine cravings in a subject is described. The method includes the step of administering to the subject by inhalation a dry powder formulation comprising between 0.1-2.0 mg of nicotine delivered as particles, at a concentration of between 0.5% and 10%, such that the subject's nicotine craving sensations are reduced at a peak nicotine blood level of less than about 5 ng/mL. In one embodiment, the nicotine particles comprise at least one nicotine salt. In another embodiment, the at least one nicotine salt is nicotine tartrate. In another embodiment, the formulation includes at least one sugar. In another embodiment, the formulation includes nicotine particles that are substantially between about 2-5 microns in size. In another embodiment, the percentage of nicotine in the formulation is about 1.5%. In another embodiment, the percentage of nicotine in the formulation is about 2.5%. In another embodiment, the percentage of nicotine in the formulation is about 5%. In another embodiment, the percentage of nicotine in the formulation is about 10%. In another embodiment, the formulation reduces nicotine cravings at a peak nicotine blood level of less than about 3.5 ng/mL. In another embodiment, the formulation reduces nicotine cravings at a peak nicotine blood level of less than about 2.5 ng/mL. In another embodiment, the formulation reduces nicotine cravings in less than about 30 seconds from inhalation. In another embodiment, the formulation reduces nicotine cravings in less than about 20 seconds from inhalation. In another embodiment, the formulation reduces nicotine cravings in less than about 15 seconds from inhalation. In another embodiment, the formulation reduces nicotine cravings in less than about 10 seconds from inhalation. In another embodiment, the formulation achieves a sensed nicotine effect in less than about 8 seconds from inhalation. In another embodiment, the formulation achieves a sensed nicotine effect in less than about 6 seconds from inhalation. In another embodiment, the formulation achieves a sensed nicotine effect in less than about 5 seconds from inhalation. In another embodiment, the formulation achieves a sensed nicotine effect in less than about 4 seconds from inhalation. In another embodiment, the formulation achieves a sensed nicotine effect in less than about 3 seconds from inhalation. In another embodiment, the formulation achieves a sensed nicotine effect prior to the nicotine reaching the brain via the bloodstream.

Also described is a kit for reducing nicotine cravings in a subject. The kit includes at least one dose of a dry powder formulation comprising between 0.1-2.0 mg nicotine particles at a concentration of between 0.5% and 10%, and an instruction material for the subject to achieve a peak nicotine blood level of less than about 5 ng/mL via inhalation of the dry powder formulation. In one embodiment, the kit further includes a second dose of the dry powder formulation that has a different amount of nicotine particles compared to the first dry powder formulation dose. In another embodiment, the kit further includes a second dose of the dry powder formulation that has a different concentration of nicotine particles compared to the first dry powder formulation dose. In another embodiment, the kit further includes a dry powder inhaler.

Also described is a dry powder formulation suitable for inhalation. The formulation includes between 0.1-2.0 mg nicotine particles at a concentration of between 0.5% and 10% nicotine particles within the formulation, wherein the nicotine particles are substantially between about 1-10 micron in size. In one embodiment, the nicotine particles are substantially between about 2-5 micron in size. In another embodiment, less than about 10% of the nicotine particles are less than about 1 micron in size. In another embodiment, less than about 10% of the nicotine particles are less than about 2 micron in size. In another embodiment, at least about 90% of the nicotine particles are less than about 10 micron in size. In another embodiment, at least about 90% of the nicotine particles are less than about 5 micron in size. In another embodiment, less than about 10% of the nicotine particles are less than about 1 micron in size and wherein at least about 90% of the nicotine particles are less than about 10 micron in size. In another embodiment, less than about 10% of the nicotine particles are less than about 2 micron in size and wherein at least about 90% of the nicotine particles are less than about 5 micron in size.

Also described is another dry powder formulation suitable for inhalation. The formulation includes a nicotine based component comprising between 0.1-2.0 mg nicotine particles at a concentration of between 0.5% and 10% nicotine particles within the formulation, wherein the nicotine particles are substantially between about 1-10 micron in size, and a cough suppressant component comprising between 0.1-5% of the formulation, wherein the cough suppressant component comprises particles substantially between about 5-10 micron in size. In one embodiment, the cough suppressant component comprises menthol or mint. In another embodiment, the nicotine based component particles are substantially between about 2-5 micron in size and the cough suppressant component particles are substantially between about 5-8 micron in size. In another embodiment, the cough suppressant component has particles substantially between about 10-200 micron in size. In another embodiment, the cough suppressant component having particles substantially between about 10-200 micron in size comprises menthol or mint. In another embodiment, the formulation includes a flavor component having particles substantially between about 10-1000 micron in size. In another embodiment, the flavor component comprises menthol or mint.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 4, comprised of FIGS. 4A and 4B, compares the relative reduction in cravings afforded by an embodiment of this invention versus a commercial product, such as Nicorette®. FIG. 4A is a chart depicting the improved properties of an exemplary formulation with 2.5% nicotine, delivering a nicotine dose of 0.5 mg in a 20 mg total formulation amount, as compared to Nicorette®, which delivers a 4.0 mg dose of nicotine. FIG. 4B is a chart depicting the improved properties of an exemplary formulation with 5% nicotine, delivering a 1.0 mg nicotine dose in a 20 mg total formulation amount as compared to the 4.0 mg nicotine dose delivered with Nicorette®.

DETAILED DESCRIPTION

Definitions

Figure 1:
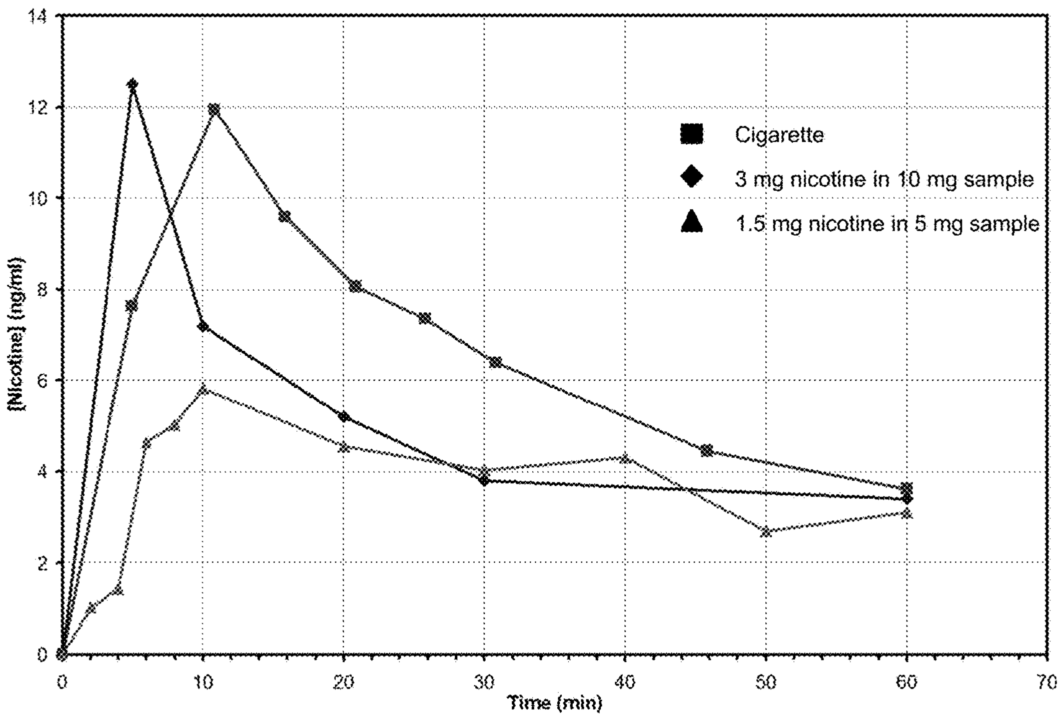
FIG. 1 is a comparative chart depicting the kinetics of blood nicotine levels achieved by cigarette smoking vs inhalation of dry powder formulations containing 3 mg and 1.5 mg nicotine doses.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein the terms "nicotine dose" and "total nicotine dose" refer to the total amount of nicotine within the total formulation amount to be delivered to a subject in order to achieve both a desired sensation of nicotine effect and a target nicotine blood concentration.

As used herein the term "formulation amount" refers to the total amount of a dry powder formulation packed in a disposable container, such as a capsule or blister pack, to be used with a dry powder inhaler, or to the total amount of a bulk dry powder formulation that can be loaded into a delivery chamber or compartment of a dry powder inhaler. The term also refers to the total amount of a dry powder formulation containing a nicotine dose to be delivered to a subject in order to achieve a particular blood nicotine concentration. Accordingly, the formulation amount includes the total dose of nicotine and may further include any additional pharmaceutically acceptable material, composition or carrier.

As used herein the term "inhalation" refers to the single act of inhaling an amount of a nicotine dry powder formulation, typically from a dry powder inhaler. The duration of an inhalation can be limited either by the control of the subject over the inhaler, such as by the physical act of continuously inhaling for a period of time and then stopping, or by a physical attribute of the inhaler.

Unless stated otherwise, the described size or size range of a particle should be considered as the mass median aerodynamic diameter (MMAD) of the particle or set of particles. Such values are based on the distribution of the aerodynamic particle diameters defined as the diameter of a sphere with a density of 1 $gm/cm^3$ that has the same aerodynamic behavior as the particle which is being characterized. Because the particles described herein may be in a variety of densities and shapes, the size of the particles is expressed as the MMAD and not the actual diameter of the particles.

The term "pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable" may also refer to a carrier, meaning a medium that does not interfere with the effectiveness of the biological activity of the active ingredient(s) and is not toxic to the host to which it is administered. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "composition" refers to a mixture of at least one compound or molecule useful within the invention with one or more different compound, molecule, or material.

As used herein, the term "craving reduction" refers to the reduction of a craving sensation in the brain. For example, a craving reduction may be recognized as a reduced or diminished desire for nicotine in a subject inhaling at least a portion of any of the dry powder formulations described herein.

As used herein, the term "sensation of nicotine effect" refers to the subjective, initial sensation experienced by a subject shortly after inhaling a formulation containing nicotine, and may occur prior to or simultaneously with the inhaled nicotine reaching the brain via the bloodstream.

As used herein, an "instructional material" includes a physical or electronic publication, a recording, a diagram, or any other medium of expression which can be used to communicate the usefulness of the composition and method of the invention for its designated use. The instructional material of the kit of the invention may, for example, be affixed to a container which contains the composition or be shipped together with a container which contains the composition. Alternatively, the instructional material may be delivered separately from the container with the intention that the instructional material and the composition be used cooperatively by the recipient.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based partly on the discovery that a dry powder formulation of micronized nicotine tartrate and lactose-containing particles within a narrow size range can significantly reduce nicotine cravings faster than traditional smoking cessation products, while maintaining lower levels of nicotine in the blood as compared to delivery of existing inhalable nicotine-based formulations. The high speed brain sensation, or nicotine effect, that can be achieved at relatively low blood nicotine levels, not only reduces nicotine cravings, but also provides health safety margins, as nicotine is known to raise blood sugar levels, which can be harmful for pre-Type II diabetics, and can also be harmful to fetuses in pregnant women who smoke. Moreover, lower nicotine levels that satisfy cravings may also reduce addiction to nicotine at a faster rate. Thus, in one aspect, the present invention provides compositions and methods related to a dry powder formulation containing a nicotine dose suitable for inhalation. In one embodiment, the formulation is comprised of nicotine particles and at least one sugar. In one embodiment, the nicotine particles are comprised of a nicotine salt. The present invention also provides methods for producing formulations of the invention.

For administration, dry powder inhalers designed specifically for delivering a powder formulation amount across multiple inhalations may be used. Examples of such dry powder inhalers can be found in co-owned U.S. Patent Application Ser. Nos. 62/147,798; 62/147,803; 62/147,806; 62/147,808; and 62/148,030, the entire disclosures of which are each incorporated by reference herein in their entirety. As contemplated herein, the dry powder formulation amount may be placed in a sealed storage chamber, such as a capsule or a blister pack, which can be loaded into any of the devices described in the aforementioned, co-owned patent applications.

The present invention is partly based on the unexpected discovery that novel formulations containing a lower dose of nicotine lead to a reduction in nicotine cravings significantly faster than traditional cigarettes or existing nicotine replacement therapies, and further achieves a faster sensation of nicotine effect in the brain than the time taken by blood to circulate from the lungs to the brain, as determined by xenon magnetic resonance imaging. In another embodiment, the uptake of nicotine within the formulation ranges from about 2 to 3 times faster than the nicotine uptake of cigarette smoke. In one embodiment, the sensing of a nicotine effect is achieved by inhalation of a formulation of the invention in less than 10 seconds. In other embodiments, the sensing of a nicotine effect is achieved by inhalation of a formulation of the invention in less than 9 seconds, in less than 8 seconds, in less than 7 seconds, in less than 6 seconds, in less than 5 seconds, in less than 4 seconds, and even in less than 3 seconds. In another embodiment, the sensing of a nicotine effect is achieved by inhalation of a formulation of the invention between about 2.68 seconds and about 8.36 seconds. As determined by xenon magnetic resonance imaging, the typical time taken by blood to circulate from the lungs to the brain falls in a time window of 5 to 10 seconds. Accordingly, the formulations of the present invention are suitable for achieving a sensed nicotine effect prior to nicotine reaching the brain from the lungs via the bloodstream, when at least a portion of the formulation is inhaled. Without being bound by any particular theory, it is believed that the nicotine formulations of the invention act, at least in part, by triggering receptors in the airways and activating neural pathways to cerebral sensation.

In one embodiment, the formulations of the invention use less than 50% of the nicotine in a standard cigarette, while achieving nicotine cravings reduction at safer blood levels of nicotine. In one embodiment, the formulation comprises about 10% nicotine. In another embodiment, the formulation comprises about 5% nicotine. In another embodiment, the formulation comprises less than 5% nicotine. In another embodiment, the formulation comprises between about 0.5-5% nicotine. In still other embodiments, the formulation comprises between 5-20% nicotine. In another embodiment, the total nicotine dose within the formulation amount is between 0.01-5 mg of nicotine. In other embodiments, the total nicotine dose within the formulation amount is between 0.1-2 mg of nicotine. In still other embodiments, the total nicotine dose within the formulation amount is about 0.5 mg of nicotine, about 1.0 mg of nicotine, about 1.5 mg of nicotine, or about 2.0 mg of nicotine. Depending on the number of inhalations desired to administer the total nicotine dose, the total formulation amount containing the total nicotine dose may be between 0.01 and 100 mg. In one embodiment, the total formulation amount containing the total nicotine dose may be between 1-20 mg. In other embodiments, the total formulation amount containing the total nicotine dose may be about 3 to 10 mg. Further, there is no limitation to the actual amount of powder inhaled per inhalation. Such amounts can be dependent on the functionality of the dry powder inhaler used, or it can be user performance dependent, where a user elects to take a shallower, or deeper, inhalation through the dry powder inhaler used. Furthermore, by administering the total dose of nicotine across multiple inhalations, the subject can more consistently insure uptake of the total dose of nicotine, as any user error occurring during a single inhalation is ultimately corrected through one or more subsequent inhalations.

In another embodiment, the present invention may further include a set of instructions for using or electing a particular formulation and formulation amount to achieve a desired level of nicotine cravings reduction. For example, the set of instructions may be conveyed to the subject in the form of an "instruction material," such as a pamphlet, manual, or any electronic file format, such as an email, web page, SMS or the like, which can further be part of a kit or associated therewith. Accordingly, the present invention may further include a nicotine therapy kit, including, but not limited to, smoke cessation kits. In one embodiment, the kit may include a plurality of formulations contained in a sealed storage chamber, such as a capsule or a blister pack. In certain embodiments, at least two of the formulation amounts have equal doses of total nicotine, but at different nicotine concentrations due to a variable total formulation amount. In other embodiments, the kit comprises at least two sets of bulk nicotine-based powder formulation having different concentrations of nicotine, and means for measuring set amounts of the powders, such as a scoop or a graduated measuring container, that can be loaded into the storage chamber of a dry powder inhaler. In other embodiments, the kit comprises a dry powder inhaler with one or more reservoirs or other compartments suitable for holding one or more bulk nicotine-based powder formulations, and further may optionally include a metering mechanism for dispensing or loading a designated amount of formulation for inhalation. In another embodiment, the kit includes pre-filled powder capsules for a set course of nicotine therapy or treatment, such as for example a 30 day course of treatment. The capsules can be filed with various amounts of powder of various nicotine concentrations and/or various nicotine doses, to achieve variable levels of nicotine cravings reduction. In other embodiments, the kit includes instructional materials which describe the steps for a method for nicotine therapy, including, but not limited to, smoke cessation therapy.

The present invention relates to dry powder formulations containing a nicotine dose, and optionally other selected materials, wherein the nicotine component and optional additional components fall within controlled particle size ranges. For example, in one embodiment, the formulation includes nicotine particles (also referred to herein as the nicotine-based component) sized substantially between about 1-10 microns, based on the MMAD of the particles. In yet another embodiment, the formulation includes nicotine particles sized substantially between about 1-7 microns. In another embodiment, the formulation includes nicotine particles sized substantially between about 2-5 microns. In yet another embodiment, the formulation includes nicotine particles sized substantially between about 2-3 microns. By selectively limiting or excluding nicotine particles below about 1 micron in size, or below about 2 microns in size, the formulations of the present invention remove or at least reduce a subject's ability to exhale nicotine back into the environment, thereby effectively reducing or removing the production of the nicotine contained in second hand smoke. Further, by selectively limiting or excluding non-respirable nicotine particles, the formulations of the present invention reduce unwanted irritation caused by nicotine particles trapped in the larger airways, oro-pharynx, the glottis vocal cords and other anatomic regions more proximal or closer to the mouth. Accordingly, in some embodiments, the smallest particles within the nicotine particle size range are at least about 1 micron, at least about 1.1 microns, at least about 1.2 micron, at least about 1.3 micron, at least about 1.4 micron, at least about 1.5 micron, at least about 1.6 micron, at least about 1.7 micron, at least about 1.8 micron, at least about 1.9 micron, or at least about 2 micron. In some embodiments, the largest particles within the nicotine particle size range are no greater than about 10 micron, no greater than about 8 micron, no greater than about 6 micron, no greater than about 5 micron, no greater than about 4.5 micron, no greater than about 4 micron, no greater than about 3.5 micron, or no greater than about 3 micron. In certain embodiments, no more than about 10% of the nicotine particles are less than about 1 micron. In certain embodiments, no more than about 10% of the nicotine particles are less than about 2 micron. In other embodiments, at least 90% of the nicotine particles are less than about 10 micron. In other embodiments, at least 90% of the nicotine particles are less than about 7 micron. In other embodiments, at least 90% of the nicotine particles are less than about 5 micron. In one embodiment, no more than about 10% of the nicotine particles are less than about 1 micron and at least 90% of the nicotine particles are less than about 10 micron. In one embodiment, no more than about 10% of the nicotine particles are less than about 1 micron and at least 90% of the nicotine particles are less than about 7 micron. In one embodiment, no more than about 10% of the nicotine particles are less than about 2 micron and at least 90% of the nicotine particles are less than about 5 micron. In one embodiment, no more than about 10% of the nicotine particles are less than about 2 micron and at least 90% of the nicotine particles are less than about 3 micron.

As would be understood by a person skilled in the art, the particle size ranges described herein are not absolute ranges. For example, a nicotine particle mixture of the present invention with a size range of about 2-5 microns can contain a portion of particles that are smaller or larger than the about 2-5 micron range. In one embodiment, the particle size value as presented for any particular component of the formulations of the present invention represents a D90 value, wherein 90% of the particles sizes of the mixture are less than the D90 value. In another embodiment, the particle size range represents a particles size distribution (PSD) wherein a percentage of the particles of the mixture lie within the listed range. For example, a nicotine particle size range of about 2-5 microns can represent a mixture of nicotine particles having at least 50% of the particles in the range of about 2-5 microns, but more preferably a higher percentage, such as, but not limited to: 60%, 70%, 80%, 90%, 95%, 97%, 98% or even 99%.

In another example, the formulation of the present invention may optionally include a cough suppressant component having particles sized substantially between 5 and 10 microns. In one embodiment, the cough suppressant component is menthol or mint. In another embodiment, the cough suppressant component may include benzocaine. It should be appreciated that the cough suppressant component can include any compound approved for suppressing cough. By selectively including menthol or mint particles between 5-10 microns, these non-respirable menthol or mint particles can reduce cough by soothing irritation in the subject's upper airways. Accordingly, in some embodiments, the smallest particles within the cough suppressant component particle size range are at least about 5 micron, at least about 6 micron, at least about 7 micron, or at least about 8 micron. In some embodiments, the largest particles within the cough suppressant component particle size range are no greater than about 10 micron, no greater than about 9 micron, no greater than about 8 micron, or no greater than about 7 micron. In certain embodiments, no more than about 10% of the cough suppressant particles are less than about 5 micron. In other embodiments, at least 90% of the cough suppressant particles are less than about 10 micron. In other embodiments, at least 90% of the cough suppressant particles are less than about 8 micron. In one embodiment, no more than about 10% of the cough suppressant particles are less than 4 micron and at least 90% of the cough suppressant particles are less than about 10 micron. In one embodiment, no more than about 10% of the cough suppressant particles are less than about 5 micron and at least 90% of the cough suppressant particles are less than about 8 micron. Although in the preferred embodiment the cough suppressant component is composed of particles substantially in the range of 5-10 micron, the cough suppressant component can comprise particles in a broader range. In one embodiment, the cough suppressant component can comprise particles in the range of 5-25 micron. In another embodiment, the cough suppressant component comprises particles substantially in the range of 5-50 micron. In yet another embodiment, the cough suppressant component comprises particles substantially in the range of 5-100 micron.

In another example, the formulation of the present invention may optionally include a cough suppressant component having particles sized substantially between 10-200 microns. This cough suppressant component can be added to the formulation instead of, or in addition to, the cough suppressant component in the range of 5-10 previously discussed. Accordingly, the formulation of the present invention can comprise two cough suppressant components, wherein each cough suppressant component has a substantially different particle size distribution. The 10-200 micron cough suppressant component may reduce a cough caused by irritation of the oro-pharynx, the glottis vocal cords and other anatomic regions more proximal or closer to the mouth that contain receptors that can trigger cough or trigger other unwanted sensations. As contemplated herein, these larger particles are substantially prohibited from entering the subglottic airways. Accordingly, in some embodiments, the smallest particles within the cough suppressant component particle size range are at least about 10 micron, at least about 12 micron, at least about 20 micron, at least about 30 micron, or at least about 50 micron. In some embodiments, the largest particles within the cough suppressant component particle size range are no greater than about 200 micron, no greater than about 150 micron, no greater than about 120 micron, no greater than about 100 micron, no greater than about 90 micron, or no greater than about 80 micron. In certain embodiments, no more than about 10% of the cough suppressant component particles are less than about 10 micron. In certain embodiments, no more than about 10% of the cough suppressant component particles are less than about 20 micron. In other embodiments, at least 90% of the cough suppressant component particles are less than about 200 micron. In other embodiments, at least 90% of the cough suppressant component particles are less than about 150 micron. In other embodiments, at least 90% of the cough suppressant component particles are less than about 100 micron. In one embodiment, no more than about 10% of the cough suppressant component particles are less than 10 micron and at least 90% of the cough suppressant component particles are less than about 200 micron. In one embodiment, no more than about 10% of the cough suppressant component particles are less than about 12 micron and at least 90% of the cough suppressant component particles are less than about 100 micron. In one embodiment, the cough suppressant component includes menthol or mint particles between about 10-200 microns in size, which may provide a soothing effect in areas of particle impact. In another embodiment, the cough suppressant component having particles between about 10-200 microns in size may include benzocaine. It should be appreciated that the cough suppressant component having particles between about 10-200 microns in size can include any compound approved for suppressing cough. In another example, the addition of at least one component in the formulation of the present invention other than the nicotine component may act to dilute the nicotine containing particles and decrease cough caused by nicotine irritating the oro-pharynx, vocal cords and other anatomic regions proximal to the trachea.

In another example, the formulation of the present invention may optionally include a flavor component having particles sized substantially between about 10-1000 microns. In one embodiment, the flavor component is composed of particles substantially in the range of about 10-200 micron. In a preferred embodiment, the flavor component is composed of particles substantially in the range of about 10-100 micron. This flavor component utilizes such embedded larger particles that may impact the subject in the oral cavity to produce a desired flavor. Further, by limiting such flavor component particles to larger than about 10 microns in size, these particles are limited in their ability to enter into the subject's lungs. Accordingly, in some embodiments, the smallest particles within the flavoring component particle size range are at least about 10 micron, at least about 12 micron, at least about 20 micron, at least about 30 micron, or at least about 50 micron. In some embodiments, the largest particles within the flavoring component particle size range are no greater than about 1000 micron, no greater than about 500 micron, no greater than about 200 micron, no greater than about 150 micron, no greater than about 120 micron, no greater than about 100 micron, no greater than about 90 micron, or no greater than about 80 micron. In certain embodiments, no more than about 10% of the flavor component particles are less than about 10 micron. In certain embodiments, no more than about 10% of the flavor component particles are less than about 20 micron. In other embodiments, at least 90% of the flavor component particles are less than about 1000 micron. In other embodiments, at least 90% of the flavor component particles are less than about 500 micron. In other embodiments, at least 90% of the flavor component particles are less than about 200 micron. In other embodiments, at least 90% of the flavor component particles are less than about 150 micron. In other embodiments, at least 90% of the flavor component particles are less than about 100 micron. In one embodiment, no more than about 10% of the flavor component particles are less than 10 micron and at least 90% of the flavor component particles are less than about 1000 micron. In one embodiment, no more than about 10% of the flavor component particles are less than 10 micron and at least 90% of the flavor component particles are less than about 200 micron. In one embodiment, no more than about 10% of the flavor component particles are less than about 10 micron and at least 90% of the flavor component particles are less than about 100 micron. In one embodiment, the flavor component is menthol. In other embodiments, the flavor component may include tobacco, mint, fruit flavors, or food grade flavorings used in candy or baking. It should be appreciated that the flavor compound may be any flavoring compound known in the art, preferably a regulatory-approved flavoring compound.

Accordingly, the formulations and methods of the present invention represent a novel product and approach to dry powder nicotine-based formulations. Unlike existing technologies which have higher nicotine concentrations, higher uptake times, higher blood nicotine levels and do not separate or segregate material components according to size, composition or other parameter, the present invention focuses on relatively low nicotine concentrations and/or nicotine dose amounts, short uptake times, fast rise in blood nicotine levels all the while maintaining low levels of blood nicotine, and selectively limits particular material components of the formulation to specific and controlled particle size ranges, thereby providing a unique and superior product that delivers respirable nicotine to the alveoli and small airways while reducing or eliminating exhaled nicotine, optionally delivers a non-respirable cough suppressant to the larger airways and/or the oro-pharynx, and optionally delivers non-respirable flavor particles to the oral cavity.

As described elsewhere herein, the formulations of the invention provide a rapid reduction in nicotine cravings while maintaining a low nicotine blood level. In one embodiment, the formulation reduces nicotine cravings at a nicotine blood level less than about 5 ng/mL. In another embodiment, the formulation reduces nicotine cravings at a nicotine blood level less than about 4.5 ng/mL. In another embodiment, the formulation reduces nicotine cravings at a nicotine blood level less than about 4.0 ng/mL. In another embodiment, the formulation reduces nicotine cravings at a nicotine blood level less than about 3.5 ng/mL. In another embodiment, the formulation reduces nicotine cravings at a nicotine blood level less than about 3.0 ng/mL. In another embodiment, the formulation reduces nicotine cravings at a nicotine blood level less than about 2.5 ng/mL. In another embodiment, the formulations of the present invention achieve nicotine cravings reduction within 3 inhalations of the product taken over 30 seconds. In certain embodiments, nicotine cravings are reduced by at least 10% within 30 seconds. In other embodiments, nicotine cravings are reduced by at least 20% within 30 seconds. In other embodiments, nicotine cravings are reduced by at least 30% within 30 seconds, by at least 40% within 30 seconds, and by at least 50% within 30 seconds. In still other embodiments, nicotine cravings are reduced by at least 10% via inhalation of less than 1 mg of nicotine over 30 seconds, or even less than 0.5 mg of nicotine over 30 seconds. In other embodiments, nicotine cravings are reduced by at least 20% via inhalation of less than 1 mg of nicotine over 30 seconds, or even less than 0.5 mg of nicotine over 30 seconds. In other embodiments, nicotine cravings are reduced by at least 30% via inhalation of less than 1 mg of nicotine over 30 seconds, or even less than 0.5 mg of nicotine over 30 seconds. In other embodiments, nicotine cravings are reduced by at least 40% via inhalation of less than 1 mg of nicotine over 30 seconds, or even less than 0.5 mg of nicotine over 30 seconds. In other embodiments, nicotine cravings are reduced by at least 50% via inhalation of less than 1 mg of nicotine over 30 seconds, or even less than 0.5 mg of nicotine over 30 seconds.

Figure 2:
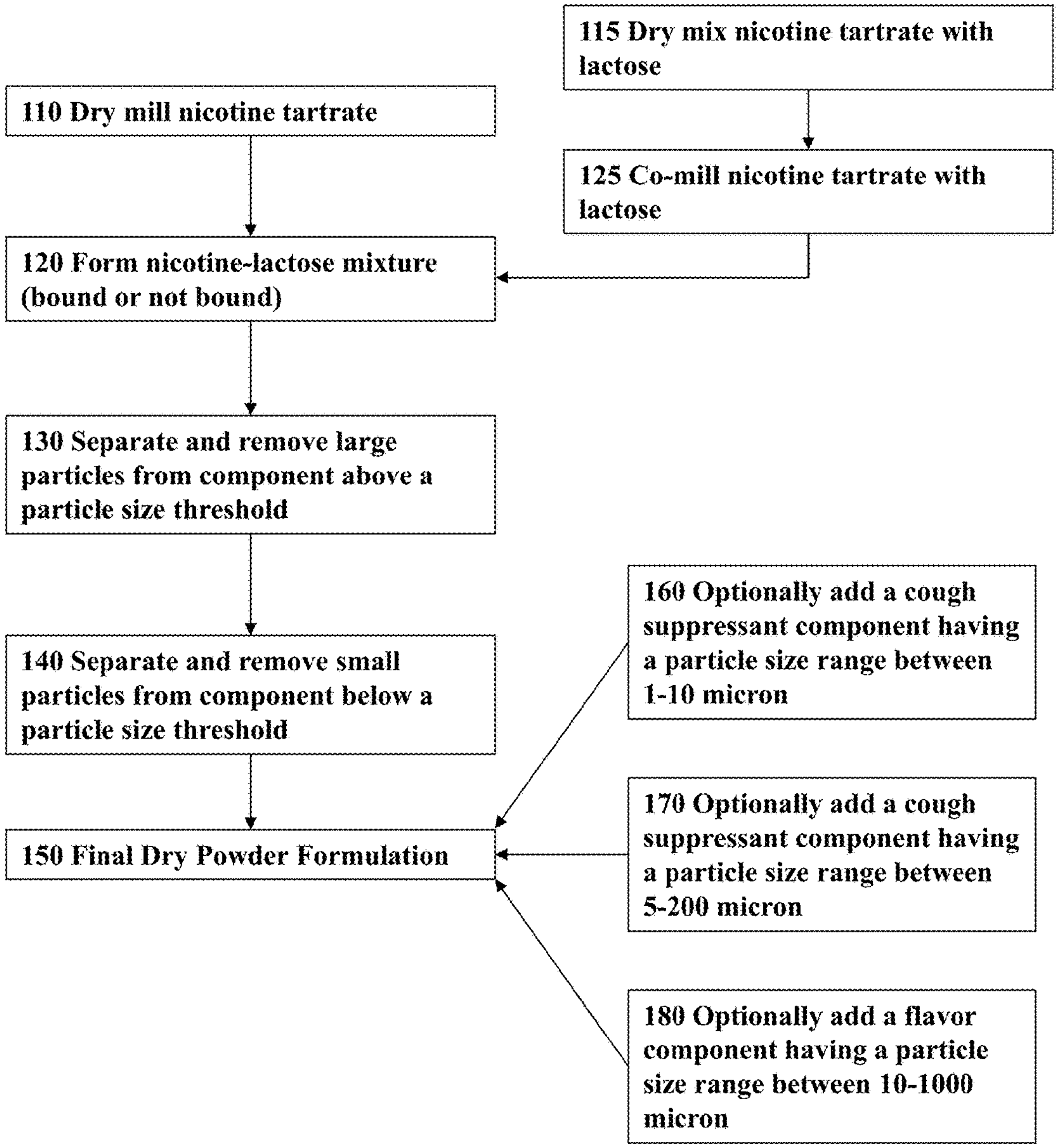
FIG. 2 is a flowchart depicting an exemplary method of manufacturing a formulation of the present invention comprising dry mixing.

As shown in FIG. 2, the present invention includes a dry process or method of producing any one of the formulations described herein. For example, in step 110, nicotine tartrate is dry milled. At step 120, nicotine is mixed with lactose. In some embodiments, the nicotine or nicotine salt is not bound to any other components of the formulation. That is the formulation contains distinct particles of nicotine or a nicotine salt, and distinct particles of other components of the formulation, such as a sugar. In one embodiment, the nicotine is not bound to the lactose particles. In other embodiments, the nicotine is bound to the lactose particles. Alternatively, nicotine tartrate and lactose may be first dry mixed, such as in step 115 and then co-milled in step 125. At step 130, the resulting nicotine particles are filtered, such as with a sieve, to remove any particles larger than a threshold size value. At step 140, the resulting nicotine particles are filtered again to remove any particles smaller than a threshold size value, resulting in the final dry powder formulation. In some embodiments, only one filtering step is needed. In other embodiments, two or more filtering steps are needed. Optionally at step 160, a cough suppressant component may be added to final formulation 150. Step 160 may contain any number of processing steps needed to obtain the desired particle size (e.g., 1-10 micron) for the cough suppressant component being added. Optionally at step 170, a cough suppressant component may be added to final formulation 150. Step 170 may contain any number of processing steps needed to obtain the desired particle size (e.g., 10-200 micron) for the cough suppressant component being added. Optionally at step 180, a flavor component may be added to final formulation 150. Step 180 may contain any number of processing steps needed to obtain the desired particle size (e.g., 10-1000 micron) for the flavor component being added.

Figure 3:
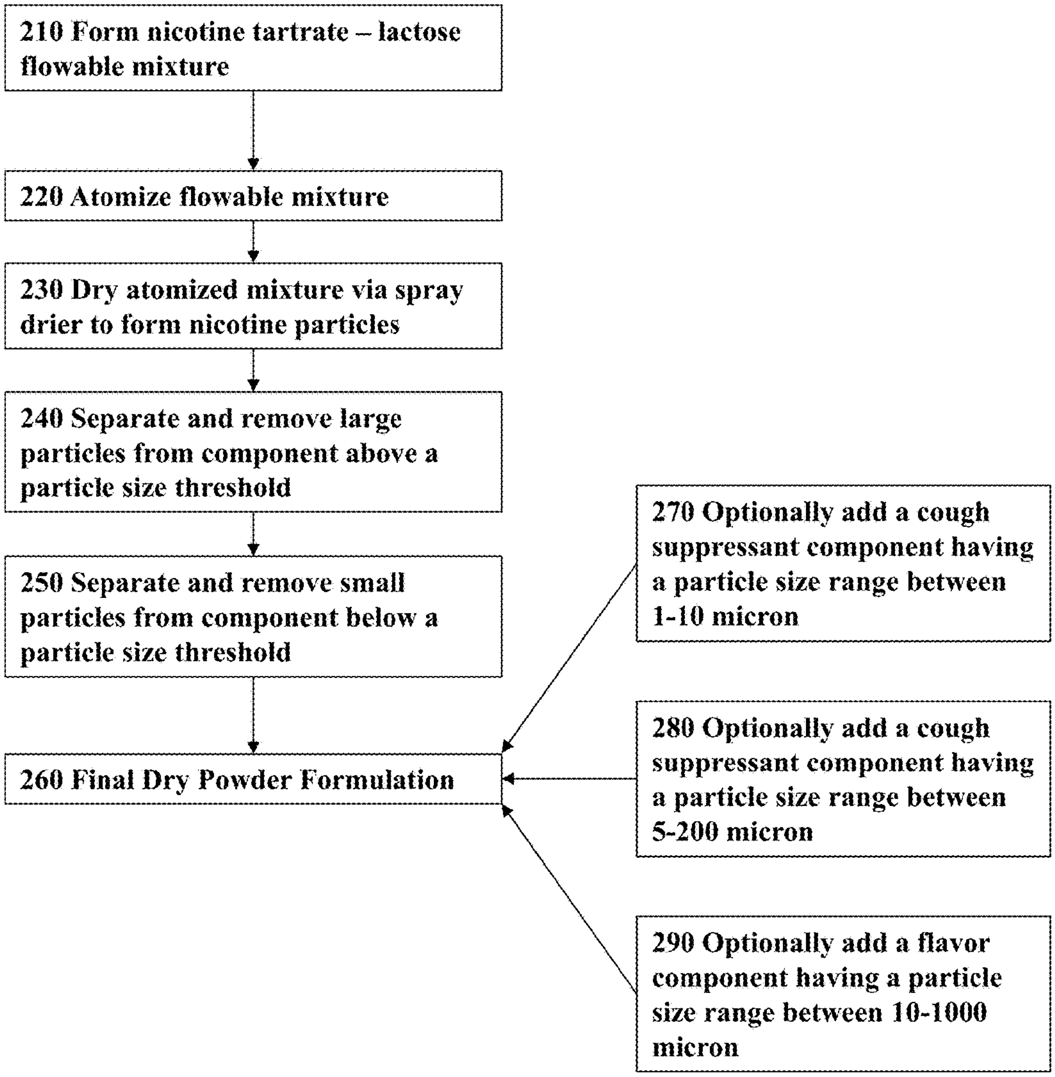
FIG. 3 is a flowchart depicting an exemplary method of manufacturing a formulation of the present invention comprising wet mixing.

As shown in FIG. 3, the present invention also includes a wet process or method of producing any one of the formulations described herein. For example, in step 210, nicotine tartrate is admixed with a carrier, such as lactose, to form a flowable mixture. At step 220, the mixture is atomized. At step 230, the mixture is dried, such as via a spray drier. Alternatively, the process may optionally be performed via fluid bed drying, wherein nicotine tartrate can instead be spray dried onto the lactose. At step 240, the resulting nicotine particles are filtered, such as with a sieve, to remove any particles larger than a threshold size value. At step 250, the resulting nicotine particles are filtered again to remove any particles smaller than a threshold size value, resulting in the final dry powder formulation. In some embodiments, only one filtering step is needed. In other embodiments, two or more filtering steps are needed. Optionally at step 270, a cough suppressant component may be added to final formulation 260. Step 270 may contain any number of processing steps needed to obtain the desired particle size (e.g., 1-10 micron) for the cough suppressant component being added. Optionally at step 280, a cough suppressant component may be added to final formulation 260. Step 280 may contain any number of processing steps needed to obtain the desired particle size (e.g., 10-200 micron) for the cough suppressant component being added. Optionally at step 290, a flavor component may be added to final formulation 260. Step 290 may contain any number of processing steps needed to obtain the desired particle size (e.g., 10-1000 micron) for the flavor component being added.

In one embodiment, the nicotine-based component may include nicotine and a pharmaceutical grade sugar prepared as solid discrete flowable particles, which may be entrained in the air inhaled by a subject so as to travel to the alveoli and smaller airways of the lungs. Further, the dried nicotine-sugar particles may be filtered, such as via one or more sieving steps, to isolate and segregate the desired particle sizes from those particles being removed.

In one embodiment, initial particles of the nicotine-based component may be produced via the methods as described in U.S. Patent Application Publication No. 20120042886, which is incorporated by reference herein in its entirety. For example, in a first step, nicotine and a pharmaceutical grade sugar, such as lactose, can be mixed with a liquid carrier so as to form a flowable mixture.

As contemplated herein, any form of nicotine may be used as the nicotine-based component. Preferably, a form of nicotine would be used which is capable of uniform dispersion throughout the composition at the lower concentrations used by the invention. Also preferably the form of nicotine used is one which achieves the fast uptake into the lungs of the patient, and ultimately the fast rise of blood nicotine levels, all the while maintaining relatively low blood nicotine levels. A form of nicotine which can be milled, or co-milled with a sugar or other components, is preferable. In another embodiment, the nicotine is blended with a sugar or other components. In one embodiment, the nicotine is a salt, which, at room temperature, is a solid. The nicotine may further be a pharmacologically active analog or derivative of nicotine or substance that mimics the effect of nicotine, either alone or in combination with other active substances. If the nicotine is a base, then it may be added to a liquid carrier, such as water, and mixed to produce a generally homogeneous liquid mixture, which can then be dried by various method to form a dry particulate formulation. In other embodiments a form of nicotine which is soluble in or miscible with a liquid carrier may also be used. For example, the nicotine may be a nicotine base, which, at room temperature, is a liquid that is miscible in water. Alternatively, the nicotine base may be an oil formulation.

Accordingly, in one embodiment, nicotine is present in the formulation as a free base. In another embodiment, the formulation may comprise a nicotine salt. In one such embodiment, the nicotine salt is nicotine tartrate. In another embodiment, the nicotine salt is nicotine hydrogen tartrate. In other embodiments, the nicotine salt can be prepared from any suitably non-toxic acid, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

As contemplated herein, the sugar is an inhalable sugar, and is generally solid at room temperature. The sugar can be milled into a particulate formulation, either by itself, or co-milled with a nicotine component. The sugar may also be soluble in a liquid carrier, such as water. Without limitation, examples of suitable sugars are lactose, sucrose, raffinose, trehalose, fructose, dextrose, glucose, maltose, mannitol, or combinations thereof. In one embodiment, the sugar is lactose. In another embodiment, the lactose is coarse lactose. In another embodiment, the sugar is alpha monohydrate lactose. The sugar may be a natural or a synthetic sugar, and may include any analogs or derivatives of sugars. It should be appreciated that any form of sugar approved as an excipient may be used as a carrier in the production of the nicotine-based component. While not required, the sugar is preferably of a pharmaceutical grade as would be understood by those skilled in the art. Preferably, the pharmaceutical grade sugar used to be milled by itself, co-milled with a nicotine component or to create the flowable mixture is a non-spheronized sugar. The pharmaceutical grade sugar may be prepared in a non-spheronized form prior to dry or wet admixture with nicotine. For example, the pharmaceutical grade sugar may be first prepared in a non-spheronized form by freeze drying, milling, micronizing or the like. In certain embodiments, the pharmaceutical grade sugar may be subjected to milling, bashing, grinding, crushing, cutting, sieving or other physical degradation process as understood by those skilled in the art, which ultimately reduces the particle size of the sugar and results in a non-spheronized sugar.

In various embodiments, the formulation can further comprise any pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. In one embodiment, the formulation is further comprised of a stabilizing agent. Each material must be "acceptable" in the sense of being compatible with the other ingredients of the formulation, including nicotine, and not injurious to the subject. Some materials that may useful in the formulation of the present invention include pharmaceutically acceptable carriers, for example sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter, lecithin and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. Other pharmaceutically acceptable materials that can be useful in the formulation include any and all coatings, antibacterial and antifungal agents, and absorption delaying agents, and the like that are compatible with the activity of nicotine or any other compound useful within the invention, and are physiologically acceptable to the subject. Supplementary active compounds, including pharmaceutically acceptable salts of those compounds, may also be incorporated into the compositions. Other additional ingredients that may be included in the compositions used in the practice of the invention are known in the art and described, for example in Remington's Pharmaceutical Sciences (Genaro, Ed., Mack Publishing Co., 1985, Easton, Pa.), which is incorporated herein by reference.

Any method of blending particles in and for the methods and formulations of the present invention is contemplated here. The blending can be conducted in one or more steps, in a continuous, batch, or semi-batch process. For example, if two or more excipients are used, they can be blended together before, or at the same time as, being blended with the pharmaceutical agent microparticles.

The blending can be carried out using essentially any technique or device suitable for combining the microparticles with one or more other materials (e.g., excipients) effective to achieve uniformity of blend. The blending process may be performed using a variety of blenders. Representative examples of suitable blenders include V-blenders, slant-cone blenders, cube blenders, bin blenders, static continuous blenders, dynamic continuous blenders, orbital screw blenders, planetary blenders, Forberg blenders, horizontal double-arm blenders, horizontal high intensity mixers, vertical high intensity mixers, stirring vane mixers, twin cone mixers, drum mixers, and tumble blenders. The blender preferably is of a strict sanitary design required for pharmaceutical products.

Tumble blenders are often preferred for batch operation. In one embodiment, blending is accomplished by aseptically combining two or more components (which can include both dry components and small portions of liquid components) in a suitable container. One example of a tumble blender is the TURBULA™, distributed by Glen Mills Inc., Clifton, N.J., USA, and made by Willy A. Bachofen A G, Maschinenfabrik, Basel, Switzerland.

For continuous or semi-continuous operation, the blender optionally may be provided with a rotary feeder, screw conveyor, or other feeder mechanism for controlled introduction of one or more of the dry powder components into the blender.

The milling step is used to fracture and/or deagglomerate the blended particles, to achieve a desired particle size and size distribution, as well as to enhance distribution of the particles within the blend. Any method of milling can be used to form the particles of the invention, as understood by one of ordinary skill in the art. A variety of milling processes and equipment known in the art may be used. Examples include hammer mills, ball mills, roller mills, disc grinders, jet milling and the like. Preferably, a dry milling process is used.

As contemplated herein, any liquid carrier may be used in the wet process. Preferably, the liquid carrier is one in which both the pharmaceutical grade sugar and the nicotine tartrate or the nicotine base are soluble. For example, in one embodiment, the liquid carrier is water. While water is the preferred liquid carrier, other liquids in combination with or in place of water may be used. For example, the liquid carrier may comprise a mixture of an alcohol and water to form an azeotropic liquid carrier. If an alcohol is used, the alcohol is preferably a primary alcohol. In one embodiment, the alcohol is preferably a lower alkyl alcohol (i.e. $C_1$ to $C_5$), such as ethanol. In such embodiments, any ratio of water to alcohol may be used, and may be determined when balancing the solubility of the mixture components with the desired drying rate of the final mixture. In some embodiments, the ratio of alcohol to water in the liquid carrier may be from about 1:1 to 1:10, preferably from about 1:2 to 1:8 and more preferably from about 1:5 to 1:7 parts by weight. Accordingly, the liquid carrier may be any liquid or liquids with which nicotine may be admixed with sugar to form a flowable mixture which is preferably of a generally uniform composition.

It should be appreciated that there are no limitations to the ratio of nicotine to sugar, or other components used, and the actual ratio used will be based on the concentration of nicotine desired in the nicotine based component particles. In one embodiment, the percentage of nicotine in the formulation is between 0.5% and 5%. In some embodiments, the percentage of nicotine in the formulation is between 1.5% and 2.5%. In other embodiments, the percentage of nicotine in the formulation is between 0.5% and 2.5%. In yet other embodiments the percentage of nicotine in the formulation is between 1.5% and 5%. In one embodiment, the percentage of nicotine in the formulation is about 2.5%. In another embodiment, the percentage of nicotine in the formulation is about 5%. In other embodiments the concentration of nicotine is between about 5-10%. In one embodiment, the percentage of nicotine in the formulation is about 10%. As such, the corresponding dose of nicotine within the formulation amount may be between 0.01-5 mg of nicotine, and may further be between 0.1-2 mg of nicotine. In one embodiment the ratio of sugar to nicotine in the dry mixture or the wet flowable mixture may vary from about 1:100 to about 100:1, or from about 3:7 to about 3:2 or alternatively, from about 4:6 parts by weight. Further, the concentration of sugar in the dry mixture or the wet flowable mixture may vary from about 1 to about 10 w/v (g/100 ml), from about 2 to about 5 w/v (g/100 ml) or from about 3% w/v (g/100 ml).

As mentioned previously, in the wet process the nicotine-sugar flowable mixture is dried, such as via a spray drier, to produce composite particles of nicotine-sugar that are suitable for delivery to the alveoli and lower airways of a subject. It should be appreciated that there is no limitation to the method of drying the flowable mixture. While a preferred method utilizes a spray drier, other drying techniques capable of producing appropriately sized particles may be used, such as fluidized bed drying. In one embodiment, the mixture is finely divided via passage through an orifice upon on entry to a spray dryer. In another embodiment, the flowable mixture may be passed through an atomizer, such as a rotary atomizer, to feed the flowable liquid into a spray dryer. Further still, any rate of drying may be used (e.g., slow or rapid rate drying), provided such rate of drying results in the formation of dry particles of the desired size range. Prior to the segregation of the desired particle size of the nicotine-based component, the resultant particles formed via the spray drier may have a particle size from about 0.1 to about 5 micron.

Additional segregation/filtering of selected particle sizes may be performed both in the dry and the wet process. In the wet process, the operating conditions of the spray dryer may be adjusted so to produce particles which are sized so as to be able to travel to the alveoli and smaller airways of the lungs. For example, a rotary atomizer may be operated at a liquid feed rate from about 2 to about 20 ml/min, or from 2 to about 10 ml/min, or from about 2 to about 5 ml/min. Further, the rotary atomizer may be operated from about 10,000 to about 30,000 rpm, from about 15,000 to about 25,000 rpm, or from about 20,000 to about 25,000 rpm. It should be appreciated that particles of various sizes may be obtained by spray drying, and particles having the desired particle size may be more specifically selected when filtered, such as via one or more sieving steps, as described elsewhere herein. The spray dryer may be operated at temperatures sufficiently high to cause the liquid carrier to rapidly evolve without raising the temperature of the sugar and nicotine within the mixture to a point at which these compounds begin to degrade. Accordingly, the spray dryer may be operated with an inlet temperature from about 120° C. to about 170° C., and an outlet temperature from about 70° C. to about 100° C.

It should be appreciated that the nicotine-based component particles may be spherical or of any other shape desired. In one embodiment of the wet process, by evolving the liquid carrier sufficiently rapidly during the spray drying process, the particles may be produced with an uneven or a "dimpled" surface. In such embodiments, the uneven surface may produce a relative turbulence as the particles travel through the air, thus providing the particles with aerodynamic lift. In such embodiments, particles having such shape may be more readily entrained, and to remain entrained, in the air inhaled by a subject, thereby improving the ability of the nicotine-based component particles to travel to the alveoli and smaller airways.

As mentioned previously, the present invention includes formulations having components characterized by particular particle size ranges. For example, the formulations of the present invention can include nicotine-based particles sized substantially between about 1-10 microns, and preferably between about 2-5 microns. In other embodiments, the formulations can optionally include a cough suppressant component (such as menthol or mint) having particles in the size range of about 1-100 microns. In other embodiments, the formulations can optionally include a second cough suppressant component having particles in the size range of about 10-200 microns. In further embodiments, the formulations can include a flavor component (such as menthol or mint) having particles in the size range of about 10-1000 microns.

As contemplated herein, the particles of the present invention can be produced in relatively narrow size ranges via the use of at least one sieving step. In such an embodiment, the sieving step includes using a sieve corresponding to the minimum or maximum of the desired particle size range to eliminate particles from the mixture that are smaller or bigger than the desired range. For example, to obtain nicotine particles in the range of about 1-5 microns, a mixture of nicotine particles produced using the milling process described herein can be provided. The mixture of nicotine particles will have a size distribution that is dependent on the milling conditions used and/or the characteristics of the input mixture to the mill. The mixture of nicotine particles can first be passed through a 5 micron sieve, wherein substantially all of the particles smaller than 5 microns pass through the sieve and are collected. The particles passing through the sieve can then transferred to a 1 micron sieve, wherein substantially all of the particles greater than 1 micron do not pass through the sieve. The particles greater than 1 micron can be collected from the sieve, wherein the collected particles will be substantially sized in the range of 1-5 microns. Accordingly, such a process can be used to narrow the range of any mixture of particles to any of the desired particle size ranges as described hereinthroughout.

In another embodiment, a mixture of particles can be provided that substantially meets either the minimum or maximum criteria of the desired particle size range. For example, if a nicotine particle size range of about 2-5 microns is desired, a mixture of nicotine particles can be provided wherein substantially all of the particles are less than 5 microns. Such a mixture can be produced by modifying the milling conditions, or when the particles are spray dried, by milling the spray dried material to result in a mixture of particles that are generally less than 5 microns. The mixture can then be transferred through a 2 micron sieve, wherein the particles not passing through the sieve are collected, and wherein the collected particles are substantially within the desired 2-3 micron range.

It is contemplated that the percentage of particles falling within the desired particle size range for any of the components of the formulation of the present invention can be dependent on the technique used to produce that component. For example, if the targeted size of the nicotine component is in the range of 2-5 micron, it is understood that greater than 90% of that component will fall within the desired range when using a spray drying production technique on a relatively small scale. However, using a relatively large scale milling production technique may only yield greater than 70% of the nicotine component within such a targeted range.

As mentioned previously, the formulation may optionally include a cough suppressant component, wherein the particles of the cough suppressant component are sized between about 5 and 10 micron. By selectively including menthol or mint particles sized between about 5-10 microns, these non-respirable menthol or mint particles can reduce cough by soothing irritation in the subject's larger airways. In another example, the formulation of the present invention may optionally include a cough suppressant component having particles sized substantially between about 10-200 microns. This cough suppressant component may reduce a cough caused by irritation of the oro-pharynx, the glottis vocal cords and other anatomic regions more proximal or closer to the mouth that contain receptors that can trigger cough or trigger other unwanted sensations. As contemplated herein, these larger particles do not enter the subglottic airways because of their momentum.

In one embodiment, the cough suppressant component of either the 5-10 or 10-200 micron ranges comprises menthol or mint. Further, it should be appreciated that any other cough suppressant compounds may be used instead of or in addition to menthol or mint, without limitation.

As contemplated herein, any form of menthol or mint, such as a solid form of menthol or mint can be used for processing into menthol or mint particles useful within the present invention. Non-limiting examples of solid forms of menthol or mint include powders, crystals, solidified distillate, flakes, and pressed articles. In one embodiment, menthol or mint is in the form of crystals. Menthol or mint can be processed into particles of a size ranging from about 5 μm to about 10 μm using any method known in the art. In some embodiments, menthol or mint is admixed with further liquid or solid additives for processing. Particulate additives can furthermore also be used. In one embodiment, menthol or mint is admixed with silicon dioxide. In another embodiment, menthol or mint is admixed with a sugar, such as lactose. In some embodiments of the wet process, the menthol or mint is processed in a liquid carrier.

As contemplated herein, any liquid carrier may be used in the process of producing the menthol or mint particles. In one embodiment, the liquid carrier is water. Preferably, the liquid carrier is one in which the menthol or mint is soluble. Accordingly, the liquid carrier may be any liquid or liquids with which menthol or mint, either alone or in combination with an additional component, forms a flowable mixture which is preferably of a generally uniform composition.

The menthol or mint flowable mixture may be dried, such as via a spray drier, to produce composite particles of menthol or mint, alone or in combination with an additional component, that are suitable for delivery to the alveoli and lower airways of a person. It should be appreciated that there is no limitation to the method of drying the flowable mixture. Examples of methods for drying the flowable mixture include, but are not limited to, spray drying, vacuum drying, and freeze drying. Further still, any rate of drying may be used (e.g., slow or rapid rate drying), provided such rate of drying results in the formation of dry particles of the desired size range.

As mentioned previously, the formulation may optionally include a flavor component, wherein the particles of the flavor component are sized between about 10 and about 1000 micron. In one embodiment, the flavor component comprises menthol or mint and may be produced as previously described herein. When other flavoring compounds are used, any known processing steps suitable for such compounds may be used to produce the flavoring component within the desired particle size range of about 10-1000 micron.

In various embodiments, the relative weight percentage of each component in the formulation of the present invention can be varied to achieve different characteristics. Thus, as one skilled in the art would understand, the relative weight percentages of the components can be modified for various reasons, for example, but not limited to: achieving better uptake of nicotine in the lungs of the patient, achieving faster blood nicotine kinetics while maintaining low concentrations, optimizing the cough suppressant performance of the formulation, varying or improving the taste of the formulation, and adjusting the relative dose of nicotine. In certain embodiments, the formulation can be about 1-20% by weight flavor component, with a preferred weight of 1-5% flavor component. In certain embodiments, the formulation can be about 1-10% by weight cough suppressant, with a preferred weight of 1-2.5% cough suppressant. In various embodiments, the remaining portion of the formulation, aside from any flavor components, cough suppressant components, carriers, or other components, is the nicotine component. In one embodiment, the formulation can be approximately 100% nicotine component.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

In a trial for assessing craving reduction, it was shown that embodiments of the invention performed significantly better than commercial products. Subjects who were administered a formulation of the invention consistently achieved a greater reduction in cravings over time as compared to subjects who were administered Nicorette®. For example, at 10 minutes after administration of a formulation of the invention containing 2.5% nicotine (based on a delivered nicotine dose of 0.5 mg within the total formulation amount), subjects taking the formulations of the invention had their cravings reduced by about 3.25, while those taking Nicorette® only had a reduction of about 2 (FIG. 4A). Similarly, subjects administered a formulation of the invention containing 5% nicotine (based on a delivered nicotine dose of 1.0 mg within the total formulation amount) had their cravings reduced by about 4.25, while those taking Nicorette® only had a reduction of about 2 (FIG. 4B). The results were scored using a visual analog scale, and a reduction score of 2.5 to 3 has been considered an adequate marker of meeting the needs of people addicted to nicotine. These results show that the formulations of the invention can very quickly exhibit such a score reduction.

The peak nicotine levels achieved in the subjects administered the two embodiments of the invention containing 2.5% and 5% nicotine respectively, were compared (Table 1). These results demonstrate that the administration of formulations of the present invention with nicotine concentrations of either 2.5% or 5% results in low peak nicotine levels in the subjects (no greater than 3.5 ng/mL), with the majority at less than 2.5 ng/mL.

TABLE 1

Trial Blood Nicotine Data

| Subject | 2.50% | Peak Nicotine | 5% | Peak Nicotine |
|---|---|---|---|---|
| 1 | 2.5 | <2.5 | 5.0 | 2.7 |
| 2 | 2.5 | 2.8 | 5.0 | 3.3 |
| 3 | 2.5 | <2.5 | 5.0 | <2.5 |
| 4 | 2.5 | <2.5 | 2.5 | <2.5 |
| 5 | 2.5 | <2.5 | 5.0 | 3.2 |
| 6 | 2.5 | <2.5 | 5.0 | <2.5 |
| 7 | 2.5 | 3 | 5.0 | 2.6 |
| 8 | 2.5 | <2.5 | 5.0 | <2.5 |

These results demonstrate that formulations of the invention containing doses of 0.5 and 1.0 mg nicotine tartrate powder reduce cravings very quickly at a low nicotine concentration and low nicotine blood level.

Example 2

Figure 5:
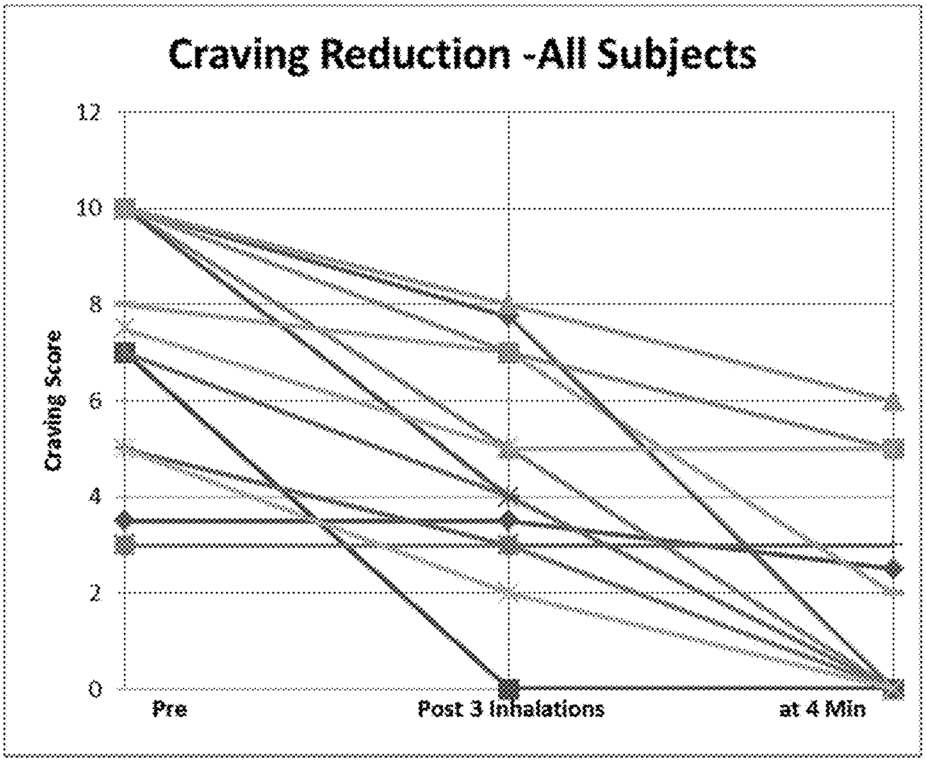
FIG. 5 is a chart depicting the relative reduction in cravings among 13 subjects after 3 inhalations of a nicotine formulation of the invention, and 4 minutes thereafter.
Figure 6:
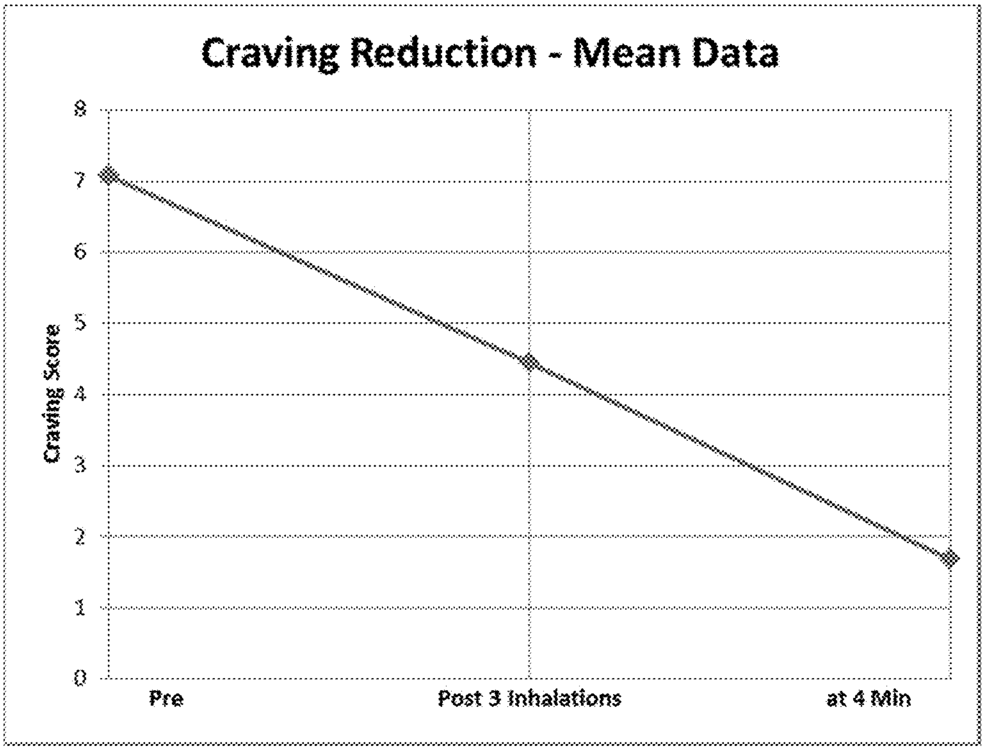
FIG. 6 is a chart depicting the mean relative reduction in cravings among 13 subjects.

As depicted in FIG. 5, a trial was conducted among 13 subjects to assess the relative nicotine craving reduction achieved upon administration of a formulation containing 2.5% nicotine (0.5 mg nicotine in a 20 mg total formulation amount). The relative craving reduction was assessed after 3 inhalations of the formulations taken over 30 seconds, and then after 4 minutes. All subjects achieved reductions in the relative level of nicotine cravings, with differences ranging from about 1 to 10 after 4 minutes. FIG. 6 is a chart depicting the mean relative reduction in cravings among the subjects. The results demonstrate that the subjects craving score was reduced from 7 before administration to about 4.5 post three inhalations, and to about 1.8 after four minutes.

Example 3

Figure 7:
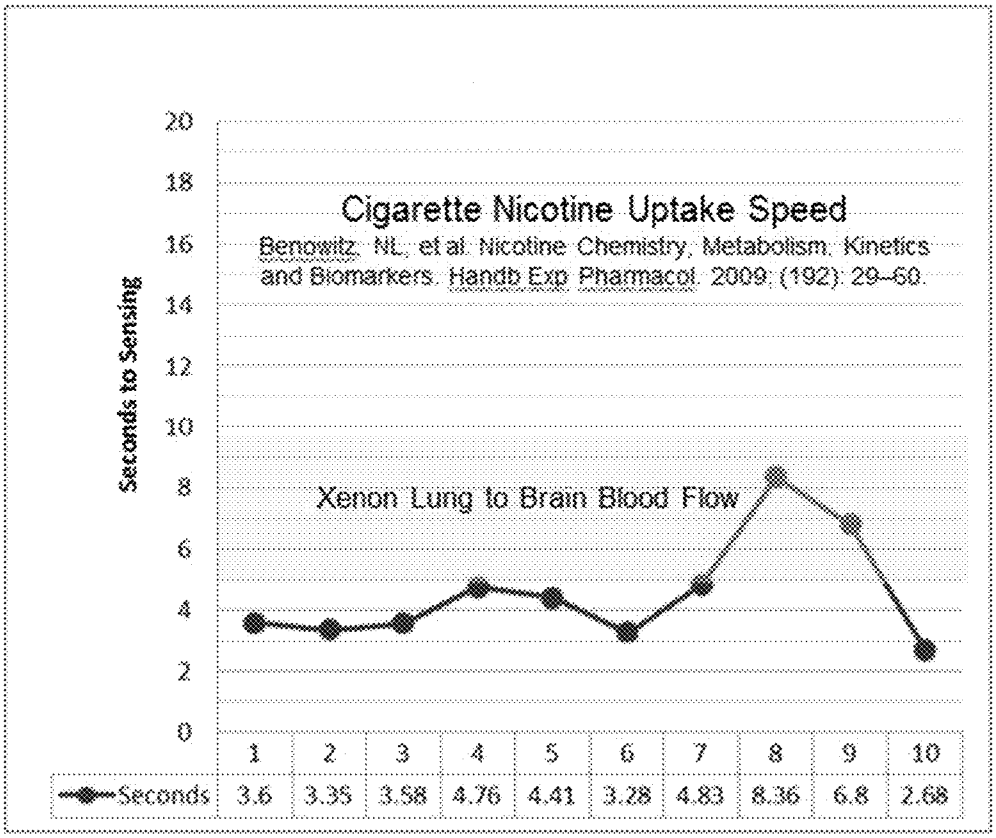
FIG. 7 is a chart depicting a sensing speed test, comparing the time between inhalation of a nicotine formulation of the invention and the subjective sensation of nicotine effect, versus the typical window of time taken by blood to circulate from the lungs to the brain as determined by xenon magnetic resonance imaging and time for average cigarette response.

As depicted in FIG. 7, a speed to sensation test was conducted, where the formulation was administered on ten separate occasions to the same subject. The testing included inhalation of a 10 mg formulation containing a 5% nicotine (0.5 mg total nicotine), which is less than 50% of the nicotine absorbed into the body from a single cigarette, and measuring the time to achieve self-reported brain sensation of nicotine, or sensing a nicotine effect. The test revealed a very rapid sensation of nicotine uptake which was 2 to 3 times faster than from a cigarette. In 6 out of 10 trials, nicotine sensation was achieved in times ranging 2.68 to 4.41 seconds, significantly lower than the time it would take blood to flow from the lungs to the brain, as determined by xenon magnetic resonance imaging. These results support the hypothesis that formulations of the invention may activate a neural pathway to cerebral sensation via receptors in the airways, since the results could not be due to nicotine reaching the brain via the blood stream. This is significantly faster than the 10-20 seconds previously reported (see Benowitz, N L et al. Nicotine Chemistry, Metabolism, Kinetics and Biomarkers. Hanb. Ex. Pharmacol. 2009; (192): 29-60)

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of reducing nicotine cravings in a subject, comprising:

administering to the subject by inhalation a dry powder formulation comprising:

between 0.1-2.0 mg nicotine particles made by spray drying a flowable mixture of nicotine salt and sugar, the nicotine salt being a salt of malic acid, and the nicotine particles having a particle size no greater than 6 μm, the formulation having a nicotine concentration of between 0.5% and 10%, wherein the administering causes a peak nicotine blood level of less than 5 ng/mL and reduces the subject's nicotine craving sensations in less than about 10 seconds from inhalation.

2. The method of claim 1, wherein the sugar is mannitol.

3. The method of claim 1, wherein the formulation comprises nicotine particles that are substantially between about 2-5 microns in size.

4. The method of claim 1, wherein the percentage of nicotine in the formulation is about 1.5%.

5. The method of claim 1, wherein the percentage of nicotine in the formulation is about 2.5%.

6. The method of claim 1, wherein the percentage of nicotine in the formulation is about 5%.

7. The method of claim 1, wherein the percentage of nicotine in the formulation is about 10%.

8. The method of claim 1, wherein the formulation reduces nicotine cravings at a peak nicotine blood level of less than about 3.5 ng/mL.

9. The method of claim 1, wherein the formulation reduces nicotine cravings at a peak nicotine blood level of less than about 2.5 ng/mL.

10. The method of claim 1, wherein the formulation achieves a sensed nicotine effect in less than about 8 seconds from inhalation.

11. The method of claim 1, wherein the formulation achieves a sensed nicotine effect in less than about 6 seconds from inhalation.

12. The method of claim 1, wherein the formulation achieves a sensed nicotine effect in less than about 5 seconds from inhalation.

13. The method of claim 1, wherein the formulation achieves a sensed nicotine effect in less than about 4 seconds from inhalation.

14. The method of claim 1, wherein the formulation achieves a sensed nicotine effect in less than about 3 seconds from inhalation.

15. The method of claim 1, wherein the formulation achieves a sensed nicotine effect prior to the nicotine reaching the brain via the bloodstream.

16. The method of claim 1, wherein the nicotine salt consists of nicotine malate and the sugar consists of mannitol.

17. The method of claim 1, wherein the flowable mixture of nicotine salt and sugar comprises a liquid carrier, and wherein the liquid carrier is water.

* * * * *